(12) United States Patent
Stigall et al.

(10) Patent No.: US 11,819,360 B2
(45) Date of Patent: Nov. 21, 2023

(54) INTRALUMINAL ROTATIONAL ULTRASOUND FOR DIAGNOSTIC IMAGING AND THERAPY

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US); Robert Emmett Kearney, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 15/998,472

(22) Filed: Aug. 15, 2018

(65) Prior Publication Data

US 2019/0053782 A1 Feb. 21, 2019

Related U.S. Application Data

(60) Provisional application No. 62/545,888, filed on Aug. 15, 2017.

(51) Int. Cl.
| | |
|---|---|
| *A61B 8/12* | (2006.01) |
| *A61N 7/00* | (2006.01) |
| *A61B 8/00* | (2006.01) |
| *A61B 8/08* | (2006.01) |

(52) U.S. Cl.
CPC ............ *A61B 8/12* (2013.01); *A61N 7/00* (2013.01); *A61B 8/0883* (2013.01); *A61B 8/0891* (2013.01); *A61B 8/445* (2013.01); *A61B 8/4488* (2013.01); *A61B 8/56* (2013.01); *A61N 2007/0043* (2013.01); *A61N 2007/0073* (2013.01); *A61N 2007/0082* (2013.01)

(58) Field of Classification Search
CPC .......... A61B 8/12; A61B 8/445; A61N 7/022; A61N 2007/0043
See application file for complete search history.

(56) References Cited

U.S. PATENT DOCUMENTS

| | | | |
|---|---|---|---|
| 4,771,774 A * | 9/1988 | Simpson | ........ A61B 17/320758 606/171 |
| 5,243,988 A | 9/1993 | Sieben | |
| 5,546,948 A | 8/1996 | Hamm | |
| 6,200,268 B1 | 3/2001 | Mnce | |
| 6,381,350 B1 | 4/2002 | Klingensmith | |
| 7,074,188 B2 | 7/2006 | Nair | |
| 7,175,597 B2 | 2/2007 | Vince | |

(Continued)

OTHER PUBLICATIONS

Shung, Diagnostic Ultrasound: Imaging and Blood Flow Measurements, 2015 (Year: 2015).*

*Primary Examiner* — Colin T. Sakamoto

(57) ABSTRACT

An ultrasound system includes an ultrasound device configured to be positioned within a body lumen of a patient. The ultrasound device includes a rotatable, flexible elongate drive cable comprising a proximal portion and a distal portion, a first ultrasound element disposed at the distal portion of the drive cable and configured to obtain imaging data of the body lumen while rotating, and a second ultrasound element disposed at the distal portion of the drive cable and configured to apply an ultrasound therapy to the body lumen while rotating. Associated devices, systems, and methods are also provided.

11 Claims, 7 Drawing Sheets

(56) References Cited

U.S. PATENT DOCUMENTS

| | | | |
|---|---|---|---|
| 7,215,802 B2 | 5/2007 | Klingensmith | |
| 7,359,554 B2 | 4/2008 | Klingensmith | |
| 7,463,759 B2 | 12/2008 | Klingensmith | |
| 8,104,479 B2 | 1/2012 | Glynn | |
| 8,403,856 B2 | 3/2013 | Corl | |
| 2002/0151799 A1* | 10/2002 | Pantages | A61M 25/00 600/466 |
| 2007/0073135 A1* | 3/2007 | Lee | A61B 8/4488 600/407 |
| 2007/0135887 A1* | 6/2007 | Maschke | A61B 8/12 623/1.11 |
| 2011/0257523 A1* | 10/2011 | Hastings | A61B 8/12 600/439 |
| 2012/0302877 A1* | 11/2012 | Harks | A61B 18/1492 600/424 |
| 2014/0005521 A1* | 1/2014 | Kohler | A61B 6/4057 600/411 |
| 2014/0180034 A1* | 6/2014 | Hoseit | A61B 18/1492 600/407 |
| 2014/0180273 A1* | 6/2014 | Nair | A61B 8/0891 606/34 |
| 2014/0207001 A1* | 7/2014 | Seo | A61B 8/4444 600/459 |
| 2014/0276050 A1* | 9/2014 | Jenson | A61B 8/085 600/439 |
| 2015/0025518 A1* | 1/2015 | Kobayashi | A61B 8/085 606/30 |
| 2015/0305708 A1* | 10/2015 | Stigall | A61B 5/02007 600/467 |
| 2019/0069949 A1* | 3/2019 | Vrba | A61B 17/122 |

* cited by examiner

INTRALUMINAL ROTATIONAL ULTRASOUND FOR DIAGNOSTIC IMAGING AND THERAPY

TECHNICAL FIELD

The present disclosure relates generally to intraluminal rotational ultrasound device and, in particular, intraluminal ultrasound device with both imaging and therapeutic functions. For example, an intraluminal ultrasound device can include both a first ultrasound transducer for imaging and a second ultrasound transducer for applying an ultrasound therapy at the distal portion of a rotating drive cable.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy with frequencies higher than 10 MHz to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Ultrasound has been used in some drug delivery and therapeutic applications. Conventionally, due to the different in operation frequencies between the two, an ultrasound imaging device and an ultrasound therapeutic device are separate and distinct. In the case of intravascular imaging and therapy, both the ultrasound imaging device and the ultrasound therapeutic device have to be inserted into and withdrawn from the patient's blood vessel at least once during a procedure workflow. To evaluate the effectiveness of an ultrasound therapy, the intravascular therapy device has to be withdrawn from the patient's blood vessel, and the imaging device has to be re-inserted in to the blood vessel. This multiplicity of insertion and withdrawal of ultrasound devices not only is time-consuming but also can increase chances of clinical complications, such as blood vessel damage.

SUMMARY

Embodiments of the present disclosure provide an ultrasound device with combined ultrasound imaging and ultrasound therapy components. For example, the ultrasound device can be rotational ultrasound device that is sized and shaped to be positioned within blood vessels of a patient or any other suitable parts of the patient body. The ultrasound imaging and ultrasound therapy components can respectively be individual ultrasound transducers that are secured adjacent to one another at the distal portion of a rotating drive cable. The ultrasound imaging transducer (e.g., an intravascular ultrasound or IVUS transducer) and the ultrasound therapy transducer operate while the rotating. The systems, devices and methods described herein advantageously allow for ultrasound imaging and ultrasound therapy components to be provided on the same device such that the multiple devices do not need to be inserted and removed for imaging and therapy. This advantageously improves the medical workflow for the patient and the physician.

According to aspects of the present disclosure, an ultrasound system is provided. The ultrasound system includes an ultrasound device configured to be positioned within a body lumen of a patient, the ultrasound device comprising: a rotatable, flexible elongate drive cable comprising a proximal portion and a distal portion; a first ultrasound element disposed at the distal portion of the drive cable and configured to obtain imaging data of the body lumen while rotating; and a second ultrasound element disposed at the distal portion of the drive cable and configured to apply an ultrasound therapy to the body lumen while rotating.

In some aspects, the first ultrasound element and the second ultrasound element each comprise a single transducer. In some aspects, the first and second ultrasound elements comprise the same transducer type. In some aspects, the transducer type comprises at least one of a piezoelectric micromachined ultrasound transducer (PMUT), a capacitive micromachined ultrasonic transducer (CMUT), a single crystal, lead zirconate titanate (PZT), or PZT composite. In some aspects, the first and second ultrasound elements comprise different transducer types. In some aspects, a center frequency of the first ultrasound element is between 10 MHz and 70 Mhz. In some aspects, a center frequency of the second ultrasound element is between 1 kHz and 5 MHz. In some aspects, the ultrasound device further comprises: a housing disposed at the distal portion of the drive cable, wherein the first ultrasound element and the second ultrasound element are positioned within the housing. In some aspects, the first and second ultrasound elements are arranged along a longitudinal axis of the drive cable. In some aspects, the first and second ultrasound elements are adjacent to one another. In some aspects, the first and second ultrasound elements are disposed on opposing sides. In some aspects, the ultrasound device further comprises: a flexible elongate sheath configured to be positioned with the body lumen, wherein the drive cable is disposed within the sheath. In some aspects, the system further comprises a movement device coupled to the drive cable, wherein movement device is configured to rotate the drive cable. In some aspects, the system further comprises a computer in communication with the first ultrasound element, wherein the computer is operable to transmit a plurality of control signals such that the first ultrasound element emits ultrasound energy at a plurality of different frequencies. In some aspects, the system further comprises a computer in communication with the second ultrasound element, wherein the computer is operable to transmit a plurality of control signals such that the second ultrasound element emits ultrasound energy at a plurality of different frequencies.

According to aspects of the present disclosure, an ultrasound method is provided. The method includes obtaining imaging data representative of a body lumen of a patient using a first ultrasound element disposed at a distal portion of a rotating flexible, elongate drive cable positioned within the body lumen; and applying an ultrasound therapy using a second ultrasound element disposed at the distal portion of the rotating drive cable.

In some aspects, the method further comprises: evaluating, at a computer in communication with the first and second ultrasound elements, the body lumen based on obtained imaging data; and determining, at the computer, a parameter for the ultrasound therapy based on the evaluating. In some aspects, the method further comprises treating the body lumen using a treatment device. In some aspects, the treating comprises introducing a pharmacological agent within the body lumen. In some aspects, the method further comprises: obtaining further imaging data of the body lumen using the first ultrasound element to evaluate the efficacy of treating the body lumen.

According to aspects of the present disclosure, an ultrasound method is provided. The method includes obtaining imaging data representative of a body lumen of a patient using a first ultrasound element disposed at a distal portion of a flexible elongate member positioned within the body lumen; determining an ultrasound therapy based on the obtained imaging data; and applying the determined ultrasound therapy using a second ultrasound element disposed at the distal portion of the flexible elongate member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
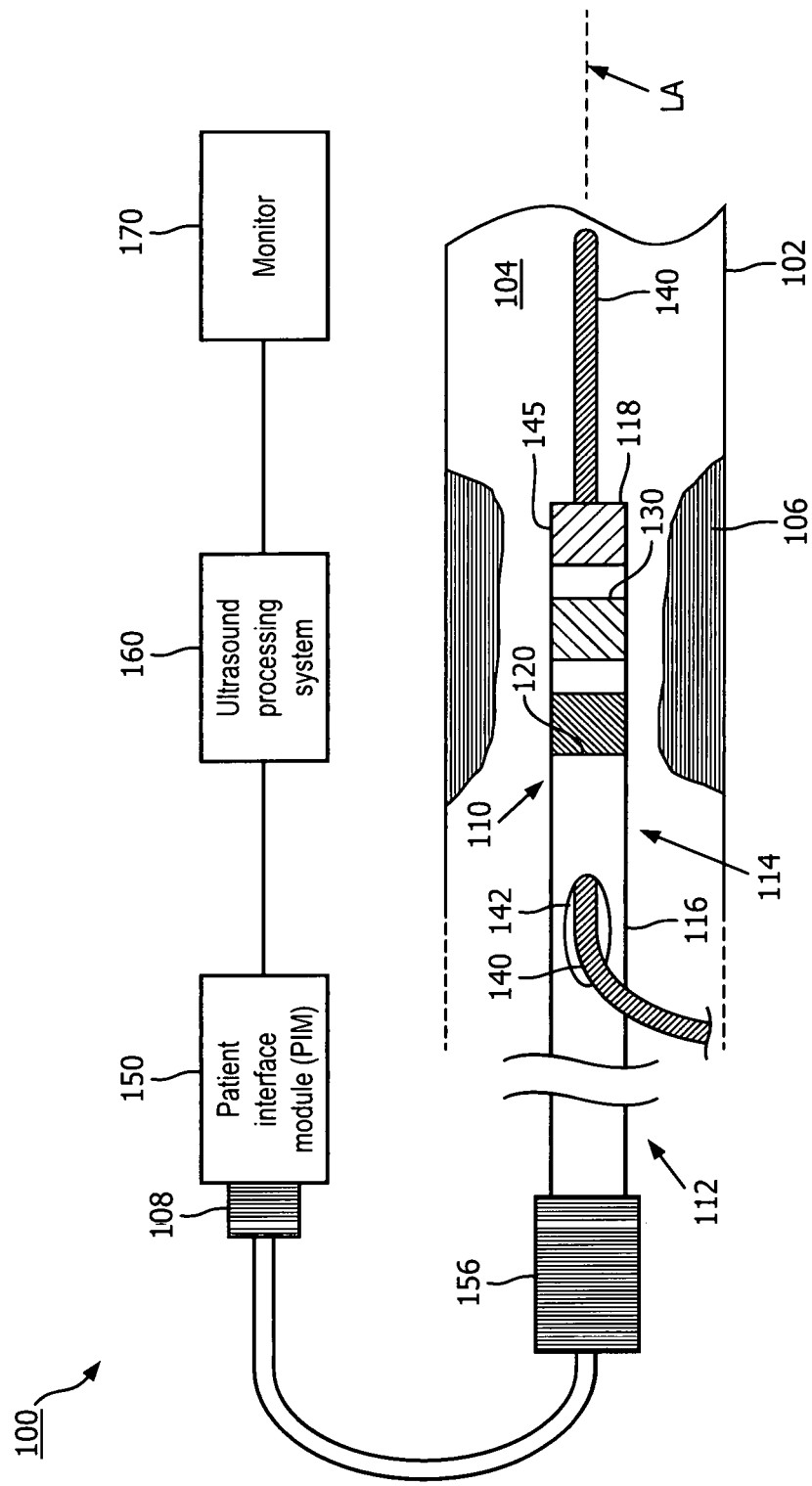
FIG. 1 is diagrammatic schematic view of an ultrasound system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The system 100 can include an ultrasound device 110, a patient interface module (PIM) 150, an ultrasound processing system 160, and/or a monitor 170. The ultrasound device 110 is structurally arranged (e.g., sized and/or shaped) to be positioned within anatomy 102 of a patient. The ultrasound device 110 obtains ultrasound imaging data from within the anatomy 102 and applies ultrasound therapy to the anatomy 102. The ultrasound processing system 160 can control the acquisition of ultrasound imaging data and/or the application of ultrasound therapy, and generates an image of the anatomy 102 (using the ultrasound imaging data received via the PIM 150) that is displayed on the monitor 170.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr and approximately 15 Fr, including values such as 3.5 Fr, 5 Fr, 7 Fr, 8.2 Fr, 9 Fr, and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the device 110. In the illustrated embodiment, the ultrasound device 110 is a catheter and includes a lumen at the distal portion 114 of the flexible elongate member 116. A guide wire 140 extends through the lumen of the catheter 110 between an entry/exit port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the exit/entry port 142 is positioned proximally of components 120, 130, and 145 of the ultrasound device 110. In some embodiments, the exit/entry port 142, the exit/entry port at the distal end 118, and/or the lumen of the ultrasound device 110 is positioned distally of the components 120, 130, and 145. In some embodiments, the ultrasound device 110 is not used with a guide wire, and the exit/entry port 142 can be omitted from the ultrasound device 110.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 includes ultrasound structures 120 and 130 at the distal portion 114 of the flexible elongate member 116. The structures 120 and 130 are configured to emit ultrasonic energy into the anatomy 102 while the device 110 is positioned within the lumen 104. In some embodiments, the two ultrasound structures 120 and 130 are distinct. In other embodiments, the two structures 120 and 130 are the same ultrasound component or part of the same ultrasound component. One of the structures 120, 130 is configured for diagnostic use, while the other of the structures 120, 130 is configured for therapeutic use. For example, the structures 120, 130 can emit different frequencies of ultrasonic energy into the anatomy 102 depending on whether the ultrasonic energy is being used for diagnosis, such as imaging, and/or treatment.

In some embodiments, the structures 120 and/or 130 include ultrasound transducer(s). For example, the ultrasound structures 120 and/or 130 can be configured to generate and emit ultrasound energy into the anatomy 102 in response to being activated by an electrical signal. In some embodiments, the structures 120 and/or 130 include a single ultrasound transducer. In some embodiments, the structures 120 and/or 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound transducer array 120 and/or 130 can be any suitable configuration, such as phased array including a planar array, a curved array, a circumferential array, an annular array, etc. For example, the ultrasound transducer array 120 and/or 130 can be a one-dimensional array or a two-dimensional array in some instances. In some instances, the structures 120 and/or 130 can be a rotational ultrasound device. The active area of the ultrasound structures 120 and/or 130 can include one or more transducer materials and/or one or more segments of ultrasound elements (e.g., one or more rows, one or more columns, and/or one or more orientations) that can be uniformly or independently controlled and activated. The active area of the ultrasound structures 120 and/or 130 can be patterned or structured in various basic or complex geometries. The structures 120 and/or 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the structures 120 and/or 130 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the array 120 and/or 130.

The ultrasound transducer(s) of the structures 120 and/or 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the structure 120 is configured to obtain ultrasound imaging data associated with the anatomy 102, such as the occlusion 106. The ultrasound imaging data obtained by the structure 120 can be used by a medical professional to diagnose the patient, including evaluating the occlusion 106 of the anatomy 102. For imaging, the structure 120 can be configured to both emit ultrasonic energy into the lumen 104 and/or the anatomy 102, and to receive reflected ultrasound echoes representative of fluid and/or tissue of lumen 104 and/or the anatomy 102. As described herein, the structure 120 can be an ultrasound imaging element, such as an ultrasound transducer and/or an ultrasound transducer array. For example, the ultrasound imaging element 120 generates and emits ultrasound energy into the anatomy 102 in response to transmission of an electrical signal to the structure 120. For imaging, the ultrasound imaging element 120 generates and transmits an electrical signal representative of the received reflected ultrasound echoes from the anatomy 102 (e.g., to the PIM 150 and/or computer 160). In various embodiments, the structure 120 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

For diagnosis and/or imaging, the center frequency of the ultrasound structure 120 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound structure 120 is tunable. For imaging, in some instances, the ultrasound structure 120 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound structure 120.

In some embodiments, the structure 130 is configured to apply an ultrasound therapy to the anatomy 102, such as the occlusion 106. For example, the structure 130 emits sound waves that damage the structure of the occlusion 106. In that regard, the device 110 and/or the structure 130 can be referenced as a lithotripsy device. The ultrasonic energy emitted by the structure 130 can create micro fractures in the calcium blockage 106. For example, the structure 130 can deliver ultrasonic energy in a targeted manner to cause cavitation (e.g., wave force cavitation, thermal cavitation, etc.) of the occlusion 106. Delivery of ultrasound therapy by the structure 130 advantageously facilitates thrombus dilution and/or vessel preparation. For example, ultrasound therapy can be applied prior to delivery of a pharmacological agent to the anatomy 102. The pharmacological agent can be a thrombolytic agent, a fibrinolytic agent, plasmin, plasmid, tissue plasminogen activator, urokinase, streptokinase, collagenace, hepranoid, anti-thrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. Accordingly, the efficacy of the treatment and the health of the patient is improved.

In some embodiments, the structure 130 is an ultrasound element, such as an ultrasound transducer and/or ultrasound transducer array. For example, the ultrasound imaging element 130 can be configured to generate and emit ultrasound energy into the anatomy 102 in response to transmission of an electrical signal to the structure 130. Unlike the structure 120, which is used of ultrasound imaging, the structure 130 need not be configured to receive ultrasonic echoes reflected the anatomy 102 and generate a representative electrical signal. For example, in some embodiments, the structure 130 is not an ultrasound element that generates ultrasound energy. Rather, the structure 130 can be an intermediate component that is configured to deliver ultrasound energy generated an ultrasound component separate from the device 110 (e.g., an external ultrasound transducer positioned outside of the body of the patient). For ultrasound therapy, the center frequency of the ultrasound structure 130 can be between 1 kHz and 5 MHz, for example, including values such as 50 kHz, 500 kHz, 1 MHz, 3 MHz, and/or other suitable values both larger and smaller. In some embodiments, the frequency of the ultrasound structure 130 is tunable. For example, the frequency of the emitted ultrasonic energy can be modified by the voltage of the applied electrical signal and/or the application of a biasing voltage to the ultrasound structure 130.

In some embodiments, such as when the structures 120 and 130 both include ultrasound transducers, the structures 120 and 130 can be configured to generate and to emit ultrasound energy, and to generate electrical signals representative of the received ultrasound echoes. One of the structures 120, 130 can be operated in diagnostic and/or imaging mode (generates and emits ultrasound energy, and generates electrical signals representative of the received ultrasound echoes), while the other of the structures 120, 130 is operated in therapeutic mode (generates and/or emits ultrasound energy).

In some embodiments, the ultrasound device 110 includes a treatment component 145. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to the anatomy 102, such as the occlusion 106. For example, the pharmacological agent can be delivered to the anatomy 102 by the treatment component 145 after the ultrasound therapy is applied to the anatomy 102 by the ultrasound structure 130. In other embodiments, the ultrasound device 110 omits the treatment component 145.

Generally, the components 120, 130, and/or 145 are positioned at the distal portion of the flexible elongate member 116. The relative positioning of the components 120, 130, and/or 145 can vary in different embodiments. In the illustrated embodiment, the diagnostic and/or imaging ultrasound structure 120 is positioned proximally of the therapeutic ultrasound structure 130. In other embodiments, the therapeutic ultrasound structure 130 is positioned proximally of the diagnostic and/or imaging ultrasound structure 120. In embodiments which include the treatment component 145, the treatment component 145 can be positioned proximally of the ultrasound structures 120 and/or 130, distally of the ultrasound structures 120 and/or 130, or between the ultrasound structures 120 and/or 130.

The ultrasound structures 120 and/or 130 can include one or more electrical conductors extending along the length from the flexible elongate member 116. The electrical conductor(s) are in communication with the ultrasound structures 120, 130 at the distal portion 114, and an interface 156 at the proximal portion 112. The electrical conductors carry electrical signals between the ultrasound processing system 160 and the ultrasound structures 120, 130. For example, activation and/or control signals can be transmitted from the computer 160 to the ultrasound structures 120, 130 via the electrical conductors. Electrical signals representative of the reflected ultrasound echoes can be transmitted from the ultrasound structures 120 and/or 130 to the computer 160 via the electrical conductors. In some embodiments, the same electrical conductors can be used for communication between the computer 160 and the ultrasound structures 120 and/or 130. In other embodiments, different electrical conductors of the device 110 can be used for communication between the computer 160 and the ultrasound structure 120, and between the computer 160 and the ultrasound structure 130.

The ultrasound device 110 includes an interface 156 at the proximal portion 112 of the flexible elongate member 116. In some embodiments, the interface 156 can include a handle. For example, handle can include one or more actuation mechanisms to control movement of the device 110, such as deflection of the distal portion 114. In some embodiments, the interface 156 can include a telescoping mechanism that allows for pullback of the device 110 through the lumen. In some embodiments, the interface 156 can include a rotation mechanism to rotate one or more components of the device 110 (e.g., the flexible elongate member 116, the ultrasound structures 120, 130). In some embodiments, the interface 156 includes a user interface component (e.g., one or more buttons, a switch, etc.) for a medical professional to selectively activate the ultrasound structure 120 for imaging or the ultrasound structure 130 for therapy. In other embodiments, a user interface component of the PIM 150, the computer 160 and/or the monitor 170 allows a medical profession to selectively activate the ultrasound structure 120 for imaging or the ultrasound structure 130 for therapy. A conduit including, e.g., electrical conductors, extends between the interface 156 and the connector 108. The connector 108 can be configured to mechanically and/or electrically couple the device 110 to the PIM 150.

The ultrasound processing system 160, the PIM 150, and/or the intravascular device 110 (e.g., the interface 156, the ultrasound structures 120 and/or 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the computer or console 160. In examples of such embodiments, the PIM 150 performs amplification, filtering, and/or aggregating of the data. In an embodiment, the PIM 150 also supplies high- and low-voltage DC power to support operation of the device 110 including circuitry associated with the ultrasound structures 120 and/or 130. The PIM 150 can be an isolation device as, in various surgical settings, patient safety requirements mandate physical and electrical isolation of the patient from one or more high voltage components.

The ultrasound processing system 160 receives imaging data (e.g., electrical signals representative of the ultrasound echo data) from the ultrasound structure 120 by way of the PIM 150. The computer 160 can include processing circuit, such as processor and/or memory. The ultrasound processing system 160 processes the data to reconstruct an image of the anatomy. The computer 160 outputs image data such that an image of the anatomy 102, such as a cross-sectional IVUS image of a vessel, is displayed on the monitor 170. The computer 160 and/or the monitor 170 can include one or more user interface elements (e.g., touchscreen, keyboard, mouse, virtual buttons on a graphical user interface, physical buttons, etc.) to allow a medical professional to control the device 110, including one or more parameters of the ultrasound structures 120, 130.

Figure 2:
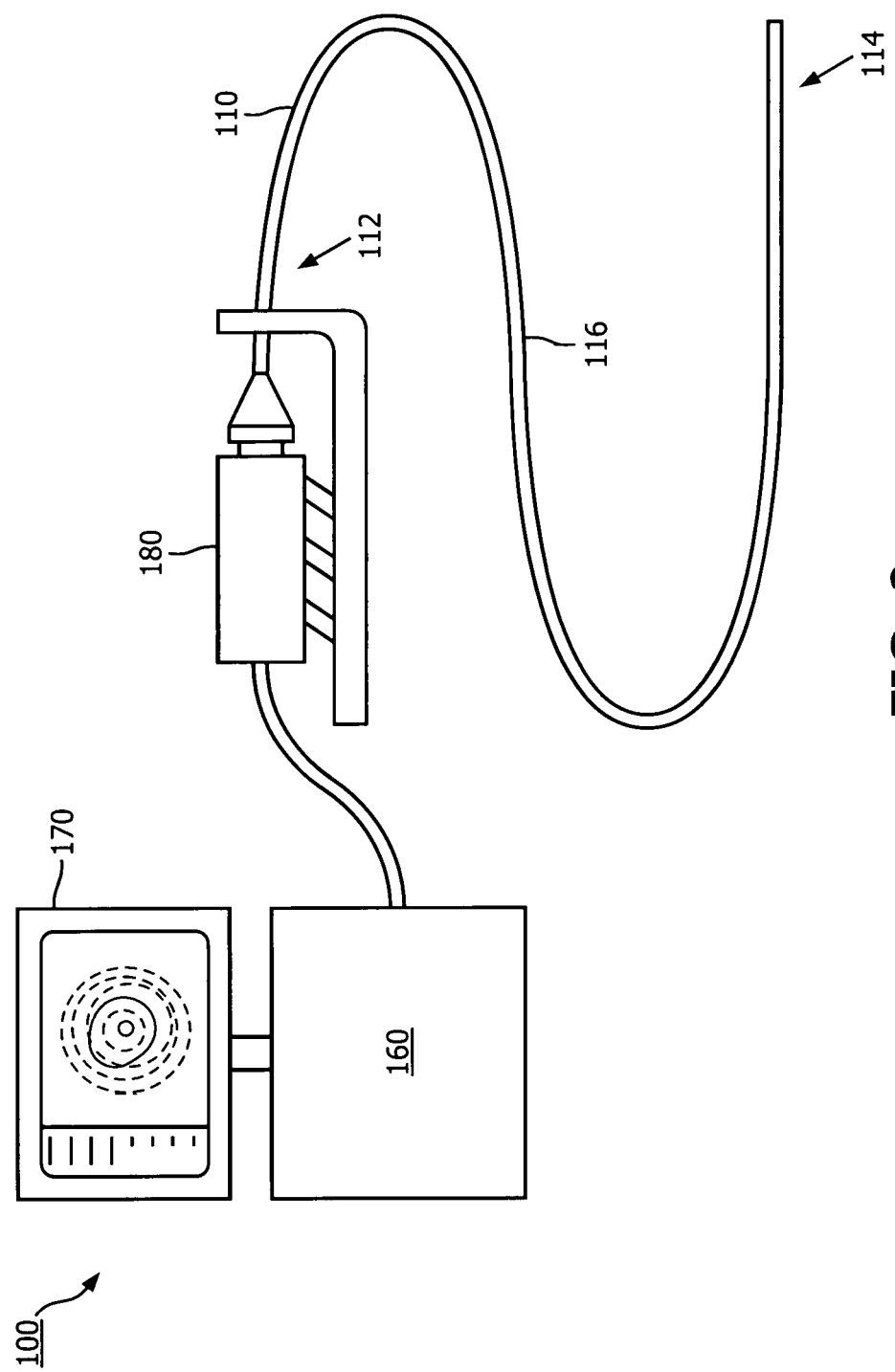
FIG. 2 is diagrammatic schematic view of an ultrasound system according to some embodiments of the present disclosure.
Figure 3:
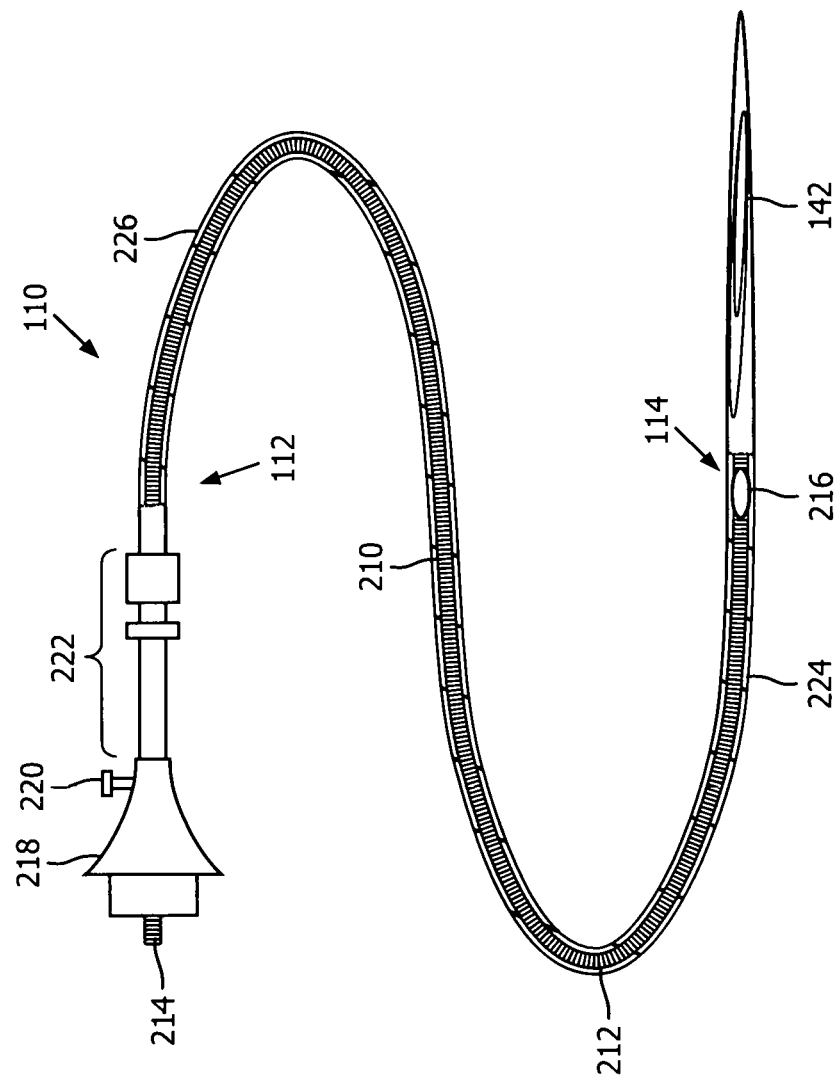
FIG. 3 is diagrammatic schematic view of a rotational ultrasound device according to some embodiments of the present disclosure.
Figure 4:
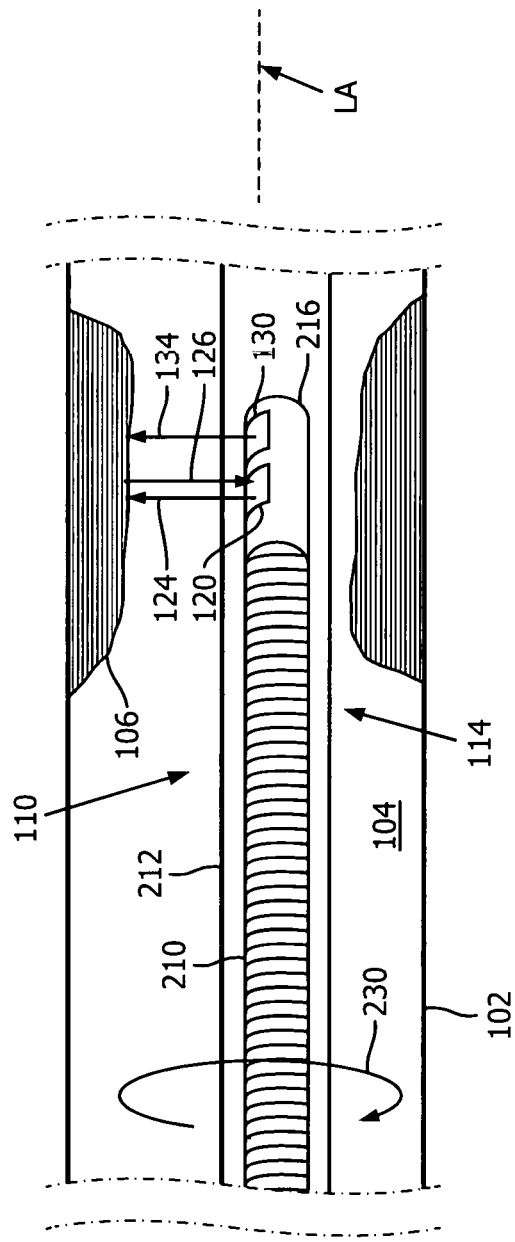
FIG. 4 is diagrammatic view of a rotational ultrasound device in situ within anatomy of a patient according to some embodiments of the present disclosure.

FIG. 2 is a diagrammatic, schematic view of the ultrasound system 100, according to an embodiment of the present disclosure. FIG. 3 is a diagrammatic, partial cutaway perspective view of the catheter 110 according to an embodiment of the present disclosure. FIG. 4 is a diagrammatic view of the catheter 110 in situ within the vessel 102.

Referring in particular to FIG. 2, in some embodiments of the present disclosure, the ultrasound system 100 is a rotational IVUS imaging and therapeutic ultrasound system. The rotational ultrasound system 100 can include the rotational catheter 110, the console or processing system 160, and the monitor 170. As discussed in greater detail herein, the catheter 110 includes the ultrasound transducer 120 for imaging and the ultrasound transducer 130 for therapy. The catheter 110 can also include circuitry associated with the transducers 120 and/or 130 mounted near the distal tip of the catheter, an electrical cable with one, two, three, four or more conductors, and the appropriate connector at the proximal portion 112 to support mechanical and/or electrical interconnection at a rotational interface. The body of the rotational catheter 110 can be referenced as the flexible elongate member 116. The distal portion 114 of the catheter 110 is positioned within the anatomy 102 of the patient. The proximal portion 112 of the catheter 110 is mechanically and/or electrically coupled to a movement device 180 of the system 100. The movement device includes one or more motors, associated circuitry, and/or other suitable components structurally arranged to impart rotational and/or longitudinal movement to one or more components of the catheter 110, such as a drive cable 210. The movement device 180 can be referenced as a pullback device and/or a sled in some instances.

In some embodiments, the movement device 180 and the PIM 150 can be combined in single device. In other embodiments, the system 100 includes a PIM 150 distinct from the movement device 180. The PIM 150 generates the required sequence of transmit trigger signals and control waveforms to regulate the operation of the circuitry associated with the transducers 120 and 130, and processes the amplified echo signals received over the conductors of the electrical cable. The PIM 150 also supplies the high- and low-voltage DC power supply to support operation of the transducers 120, 130. In that regard, the PIM 150 is structurally arranged to DC supply voltages to the circuitry of the catheter 110 across a rotational interface, using slip rings and/or the implementation of the active spinner technology described in U.S. Pat. No. 8,403,856, which is hereby incorporated by reference in its entirety. In some embodiments, the PIM 150 supplies AC voltage to the transducers 120, 130 using, e.g., a rotary transformer.

FIGS. 3 and 4 illustrate additional detail regarding the structure of the rotational ultrasound catheter 110. FIG. 4 also shows the catheter 110 in situ in the anatomy 102. In some respects, the catheter 110 is similar to rotational IVUS catheters such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the rotational catheter 110 includes an imaging core 210 and an outer catheter/sheath assembly 212. The imaging core 210 includes a flexible drive cable or shaft that is terminated at the proximal end of the proximal portion 112 by a rotational interface 214 providing electrical and mechanical coupling to the PIM 150. The imaging core 210 can also include one, two, three, four, or more electrical conductors in communication with the transducers 120, 130. The distal portion 114 of the flexible drive shaft of the imaging core 210 is mechanically coupled to a proximal portion of a transducer housing 216 containing the transducers 120 and 130, and associated circuitry, as described in more detail herein.

The catheter/sheath assembly 212 includes a hub 218 that supports the rotational interface 214 and provides a bearing surface and a fluid seal between the rotating and non-rotating elements of the catheter 110. The hub 218 includes a luer lock flush port 220 through which saline is injected to flush out the air within the sheath 212 and fill the inner lumen of the sheath 212 with an ultrasound-compatible fluid at the time of use of the catheter 110. The saline or other similar flush is typically required since air does not readily conduct ultrasound. Saline also provides a biocompatible lubricant for the rotating drive cable of the imaging core 210. The hub 218 is coupled to a telescope 222 that includes nested tubular elements and a sliding fluid seal that permit the catheter/sheath assembly 212 to be lengthened or shortened to facilitate axial or longitudinal movement of the transducer housing within an acoustically transparent window 224 of the distal portion of the catheter 110. In some embodiments, the window 224 is composed of thin-walled plastic tubing fabricated from material(s) that readily conduct ultrasound waves between the transducer and the vessel tissue with minimal attenuation, reflection, or refraction. A proximal shaft 226 of the catheter/sheath assembly 212 bridges the segment between the telescope 222 and the window 224, and is composed of a material or composite that provides a lubricious internal lumen and optimum stiffness, but without the need to conduct ultrasound. The guidewire entry/exit port 142 is provided at the distal portion of catheter 110 in the illustrated embodiment.

The movement device 180 rotates the drive cable of the imaging core 210 (e.g., in a clockwise or counter-clockwise direction 230) inside the polymer/plastic sheath 212 inserted into lumen 104 of the anatomy 102. Rotation of the drive cable 210 causes corresponding rotation of the housing 216, which is mechanically coupled to the drive cable. The transducers 120 and 130 are fixedly secured to the housing 216, and correspondingly rotate with the drive cable 210. The transducer elements 120, 130 are oriented such that the respective ultrasound beams 124, 134 propagate generally perpendicular to the longitudinal axis LA of the catheter 110. The fluid-filled sheath 212 protects the tissue of the anatomy from the spinning transducers 120, 130 and the driveshaft 210 while permitting ultrasound signals to freely propagate. As the driveshaft rotates (e.g., at 30 revolutions per second), the transducers 120, 130 are selectively and/or periodically excited with a high voltage pulse to emit a burst of ultrasound energy. The ultrasonic energy emitted by transducer 130 applies ultrasound therapy 134 within the anatomy 102, including the occlusion 106. For imaging, the transducer 120 listens for the returning ultrasound echoes 126 reflected from various tissue structures of the anatomy 102, such as the occlusion 106. Based on the IVUS imaging data obtained by the transducer 120, the IVUS imaging system 160 assembles a two-dimensional image of the vessel cross-section from a sequence of several hundred of these ultrasound pulse/echo acquisition sequences occurring during a single revolution of the transducer 120.

Figure 5:
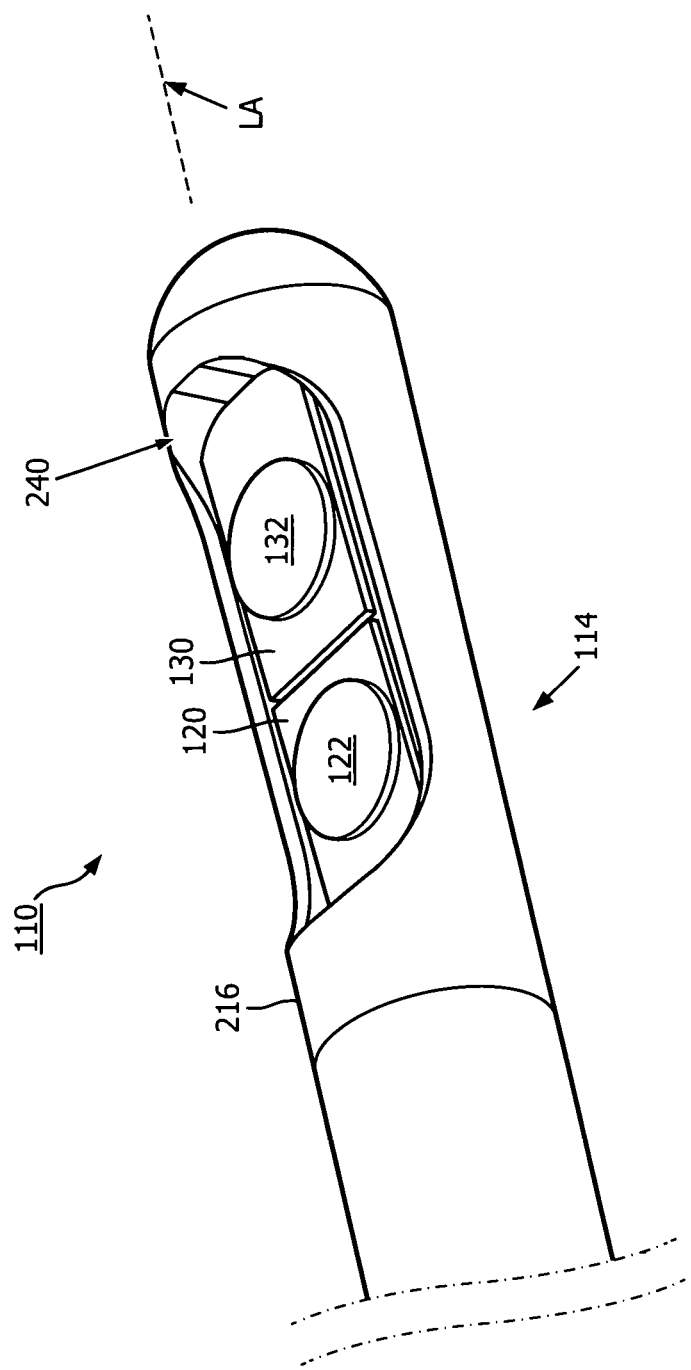
FIG. 5 is diagrammatic perspective view of a distal portion of a rotational ultrasound device in according to some embodiments of the present disclosure.
Figure 6:
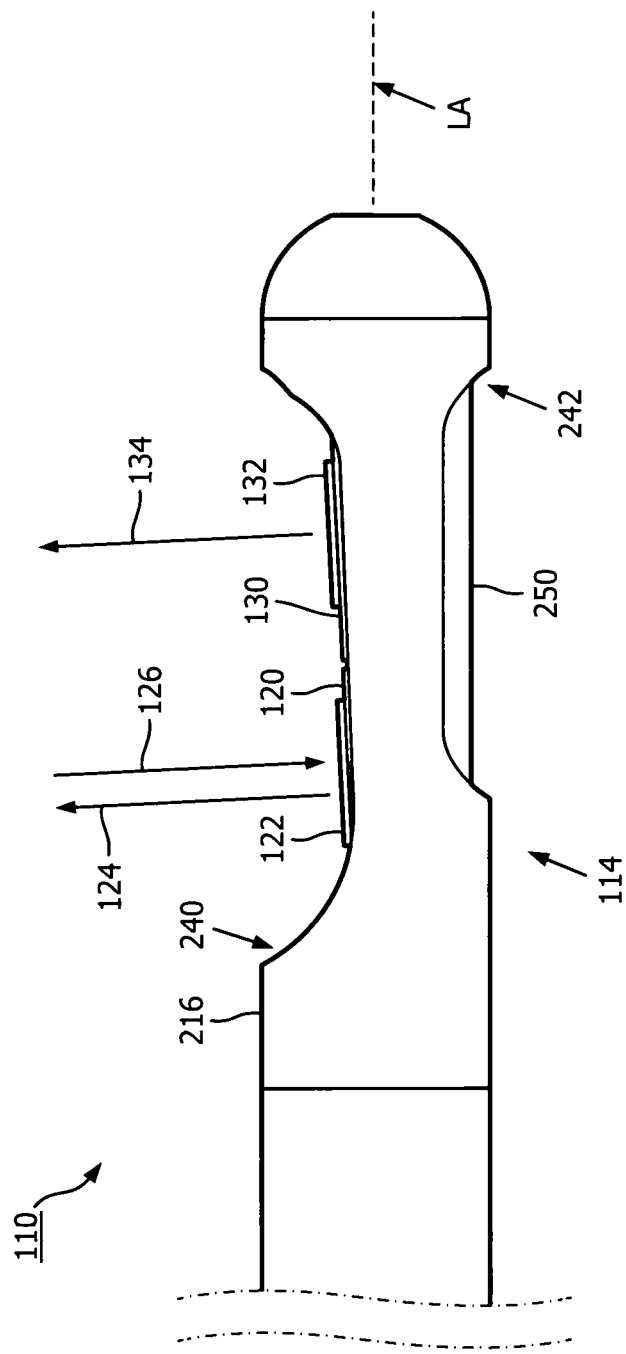
FIG. 6 is diagrammatic side view of a distal portion of a rotational ultrasound device in according to some embodiments of the present disclosure.

FIG. 5 is diagrammatic perspective view of the transducer housing 216 at the distal portion 114 of the catheter 110. FIG. 6 is diagrammatic side view of the transducer housing 216 at the distal portion 114 of the catheter 110. The ultrasound elements 120 and 130 are fixedly secured to the housing 216 such that rotation 230 of the imaging core 210 and the housing 216 causes rotation 230 of the ultrasound elements 120 and 130. In that regard, the ultrasound element 120 is structurally arranged and/or otherwise configured to obtain imaging data while rotating. In ultrasound element 130 can be is structurally arranged and/or otherwise configured to apply an ultrasound therapy while rotating. In that regard, the ultrasound elements 120, 130 can emit and/or receive ultrasound energy during all or portions of the circumference of revolution of the drive cable 210. For example, the emitting ultrasound energy from the ultrasound element 130 during only a portion of the revolution of the drive cable 210, the ultrasound therapy can be applied to selected portions of the anatomy 102.

The ultrasound elements 120 and 130 are mechanically coupled to the housing 216 using any suitable attachment mechanism, such as adhesive, welding, soldering, etc. The ultrasound elements 120 and 130 are positioned adjacent to one another along the longitudinal axis LA. In some instances, the ultrasound elements 120 and 130 can be referenced as being aligned in series. The ultrasound element 120 can be proximal to the ultrasound element 130, as shown in the illustrated embodiment, or the ultrasound element 130 can be proximal to the ultrasound element 120. In some embodiments, the ultrasound elements 120 are positioned side-by-side along an axis perpendicular to the longitudinal axis LA. In some embodiments, the ultrasound elements 120, 130 are disposed on opposite sides of the housing 216. For example, in the orientation of the housing 216 illustrated in FIG. 6, one of the elements 120, 130 can be disposed on one side of the housing 216 (e.g., facing up), while the other of the elements 120, 130 can be disposed on the opposing side of the housing 216 (e.g., facing down). For example, the ultrasound elements 120, 130 can be configured to emit ultrasound energy in opposite directions. In the illustrated embodiment, the ultrasound elements 120 and 130 are individual ultrasound elements. In other embodiments, the ultrasound elements 120 and/or 130 can be a one or two dimensional ultrasound array including two or more ultrasound transducers.

The ultrasound elements 120 and 130 include active areas 122, 132, respectively. For example, the active areas 122, 132 are representative of the ultrasound transducers. The transducers 122, 132 can be suitable shape, including circular as shown in the illustrated embodiment. Generally, the transducers 122 and/or 132 can be PMUTs, CMUTs, single crystals, PZTs, PZT composites, other suitable transducer type, and/or combinations thereof. In some embodiments, both the transducers 122 and 132 are the same transducer type (e.g., both transducers 122 and 132 are PMUT, CMUT, single crystal, PZT, PZT composite, etc.). Using the same transducer type may advantageously simplify manufacturing and/or implementation for control electronics, electrical wires for communication, etc. In other embodiments, the transducers 122 and 132 are different transducer types (e.g., transducer 122 is CMUT and the transducer 132 is PZT, etc.). Using different transducer types may advantageously allow for transducer types that are optimized for a given purpose to be used. For example, CMUT may be advantageously implemented for the imaging transducer 120 to utilize its higher frequency spectrum. PMUT may be advantageously implements for the therapeutic transducer 130 to utilize its lower frequency spectrum.

The ultrasound element 120 can be structurally arranged and/or otherwise configured (e.g., material of the transducer, thickness of one or more components of the transducer, etc.) to have a relatively higher center frequency than the ultrasound element 130. Similarly, the ultrasound element 130 can be structurally arranged and/or otherwise configured (e.g., material of the transducer, thickness of one or more components of the transducer, etc.) to have a relatively lower center frequency than the ultrasound element 120. In some embodiments, the ultrasound elements 120, 130 can transmit and/or receive at varying frequencies. For example, the ultrasound elements 120, 130 can be driven at different operating voltages to change the frequency of the emitted ultrasound energy. In some embodiments, the ultrasound element 120 can be tuned to receive ultrasound echoes associated with different frequencies. In this manner, for example, the ultrasound elements 120, 130 can be tunable. The ultrasound elements 120, 130 can be configured to emit and/or receive ultrasound energy associated with a first frequency range and a second frequency range, respectively. The first frequency range and the second frequency range can overlap in some embodiments. In other embodiments, the first frequency range and the second frequency range have no overlap or common frequencies.

The housing 216 can include one or more electronic components to control the ultrasound elements 120, 130 to emit ultrasound energy and/or receive ultrasound echoes. For example, one or more controllers (e.g., ASICs) described herein can disposed within the housing 216. A single or multiple electrical cables can be used to connect the elements 120, 130 to the PIM 150, ultrasound processing system 160, etc. For example, one or more cables can be used to facilitate electrical communication between the ultrasound transducer 120 and the PIM 150, computer 160, etc. One or more cables can be used to facilitate electrical communication between the ultrasound transducer 120 and the PIM 150, computer 160, etc. In some embodiments, the same cables are in communication with both the ultrasound transducers 120, 130, the PIM 150, and the computer 160. The ultrasound transducers 120, 130 can be operated by a user using the interface 156, the PIM 150, and the computer 160 (e.g., physical controls, such as a button, switch, etc., GUI elements on touchscreen, etc.). For example, the ultrasound transducers 120, 130 can be controlled to operate so that they do not interfere with one another. For example, ultrasound imaging transducer 120 can be operated separately from the therapeutic transducer 130 such that the ultrasound therapy emissions of the transducer 130 do not interfere with the imaging echoes associated with the transducer 120.

The housing 216 can be formed of a metal, metal alloy, polymer, plastic, other suitable material, and/or combinations. The housing 216 can be generally cylindrically shaped, with cutouts 240 and/or 242. The transducers 120 and 130 are positioned within space of the housing 216 defined by the cutouts 240 and/or 242. An acoustic backing material 250 can be disposed within the cutout 242 of the housing 216 to block, dampen, and/or otherwise impede transmission of sound waves in undesired directions (e.g., opposite the directions indicated by ultrasound energy 124, 134). An acoustic matching material can be positioned within the cutout 240 between, surrounding, and/or covering the transducers 120, 130. The acoustic matching material can be configured to facilitate and/or other improve transmission of acoustic energy from the ultrasound transducers 120, 130 (e.g., as indicated by the emitted ultrasound energy 124, 134 and the reflected ultrasound echoes 126).

A rotational ultrasound device 110 can be advantageously utilized with a movement device 180 (e.g., pullback device) to facilitate intraluminal imaging and/or therapy while the ultrasound device is pulled back (e.g., longitudinally moved) through the body lumen at set speeds. Some medical professionals may also prefer the using the rotational ultrasound device. Rotational ultrasound devices can also operate at a higher frequency, which can advantageously allow for higher quality intraluminal images (e.g., IVUS images) to be obtained relative to other ultrasound imaging types. Rotational imaging also advantageously minimizes and/or eliminates imaging artifacts such as sidelobes, grating lobes, and poor elevation focus (perpendicular to the imaging plane) relative to other ultrasound imaging types.

Figure 7:
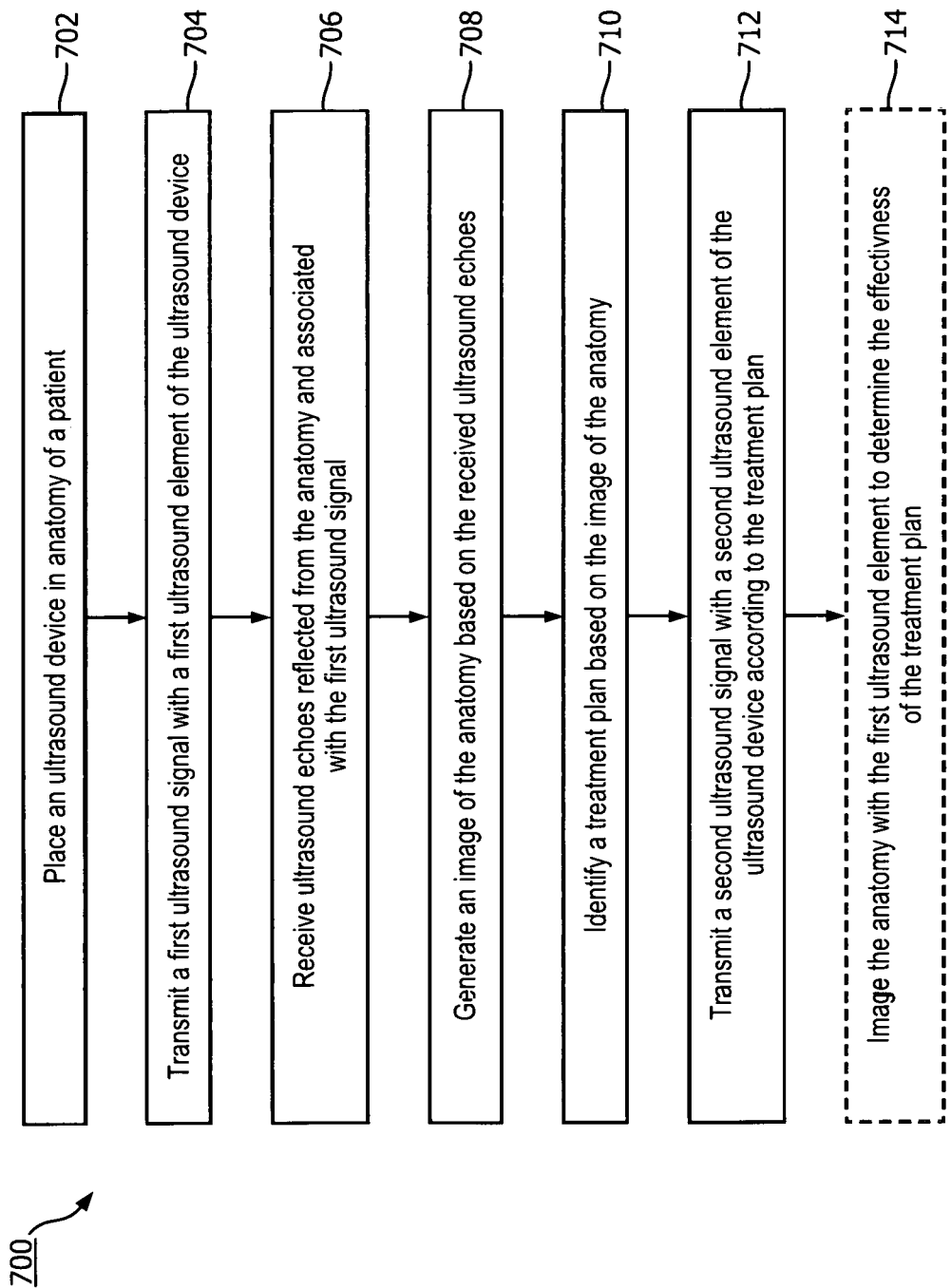
FIG. 7 is a flow diagram of an ultrasound imaging and ultrasound therapy method according to embodiments of the present disclosure.

FIG. 7 provides a flow diagram illustrating a method 700 of transmitting ultrasound signals. As illustrated, the method 700 includes a number of enumerated steps, but embodiments of the method 700 may include additional steps before, after, and in between the enumerated steps. In some embodiments, one or more of the enumerated steps may be omitted, performed in a different order, or performed concurrently. The method 700 may be performed using any of the systems and devices referred to in FIGS. 1-6.

At step 702, the method 700 may include positioning an ultrasound device in anatomy of a patient. For example, the ultrasound device may be a combined intravascular ultrasound (IVUS) imaging and ultrasound therapy device. The ultrasound device may be ultrasound device 110 including the ultrasound elements 120, 130. For example, the ultrasound device can be a rotational ultrasound device with an imaging ultrasound transducer element and a therapeutic ultrasound element at the distal portion of a rotating drive cable. The step 702 can include placing a sheath and the imaging core/drive cable within the lumen of the anatomy. The drive cable can be disposed within the sheath of the ultrasound device.

At step 704, the method 700 may include transmitting a first ultrasound signal with a first ultrasound element of the ultrasound device. The first ultrasound signal can be associated with ultrasound imaging in some embodiments. Step 704 can be performed while the drive cable of the ultrasound device and the first ultrasound element are rotating within the sheath positioned inside anatomy. In that regard, the method 700 can include connecting the ultrasound device and/or the drive cable to a movement device, such as a pullback device, that is configured to rotate and/or longitudinally translate the ultrasound device. The first ultrasound signal may be reflected off the anatomy (e.g., tissue, blood vessel, plaque, etc.) in the form of ultrasound echoes, some of which may travel back toward the first ultrasound element.

At step 706, the method 700 may include receiving ultrasound echoes reflected from the anatomy and associated with the first ultrasound signal. The ultrasound echoes may be received by the same ultrasound element that transmitted the first ultrasound signal. In some embodiments, the data from the ultrasound echoes may be analyzed by a controller within the ultrasound device (such as adjacent to the first and/or second ultrasound elements) or communicated by a cable or other component to a processing device outside the patient. In some embodiments, the steps 704 and/or 706 can be referenced as obtaining imaging data using the first ultrasound element.

At step 708, the method 700 may include generating an image of the anatomy based the received ultrasound echoes. The image of the anatomy may be a two- or three-dimensional image of the anatomy. In some embodiments, the image of the anatomy is displayed on a display device such as a computer monitor. For example, the image can be IVUS image of a blood vessel in some embodiments.

At step 710, the method 700 may include identifying a treatment plan based on image of the anatomy. In some embodiments, the image of the anatomy may be analyzed by the system automatically to detect problems (i.e., calcification, occlusions, plaques, abnormalities in the anatomy, etc.). The system may be used to identify a treatment plan based on problems in the image. In some embodiments, the treatment plan may include a therapeutic procedure to be performed by the ultrasound device. The method 700 can include evaluating the anatomy based on the obtained image data (steps 704, 706) and/or the generated imaging (e.g., step 708). For example, the diameter & calcification of the blood vessel can be determined using, e.g., virtual histology (VH) and/or other suitable algorithms. In general, a target site, such as occlusion 106 tends to reflect more ultrasound energy when it has a higher level of calcification. That is, by measuring the intensity of the ultrasound signal associated with ultrasound echoes reflected from the target site, the level of calcification of the target site can be determined. For example, the method 700 can include determining the density of an occlusion in the lumen, the age and/or hardness of the calcium in the vessel plaque, etc. The method 700 and/or step 710 can include determining one or more ultrasound parameters for ultrasound therapy. For example, the optimal frequency, pulse amplitude, pulse length, and/or other suitable parameters for ultrasound cavitation/vessel preparation with the second ultrasound element can be determined in an automated process by the computer or by a medical professional. After the ultrasound processing system 160 determines the set of ultrasound parameters, the ultrasound processing system 160 can transmit an electrical signal representative of the parameters to the ultrasound transducer 130 such that the ultrasound transducer 130 operates based on the parameters.

Detecting and characterizing plaque using IVUS with VH are described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

At step 712, the method 700 may include transmitting a second ultrasound signal with a second ultrasound element of the ultrasound device. In that regard, the second ultrasound signal can be associated with therapy of the anatomy in which the ultrasound device is positioned. Step 712 can be performed while the drive cable of the ultrasound device and the second ultrasound element are rotating within the sheath positioned inside anatomy. Between steps 704 and 712, the method 700 and associates systems and devices switch from imaging mode to a therapy mode to facilitate treatment of the diseased area, cavitation, thermal or ultrasound/vessel preparation, with the parameters determined in step 710. The second ultrasound element may be adjacent to the first ultrasound element. In some embodiments, the second ultrasound element is configured to transmit ultrasound signals but not receive ultrasound signals. The second ultrasound signal may have a frequency lower than that of the first ultrasound signal. In some implementations, the second ultrasound signal is transmitted to perform a therapeutic procedure such as creating micro fractures in the anatomy and/or treating the anatomy in preparation for delivery of a drug.

At step 714, the method 700 may optionally include imaging the anatomy with the first ultrasound element to determine the effectiveness of the treatment plan. In some embodiments, the first ultrasound element may be used to transmit another ultrasound signal and receive the reflected ultrasound echoes to determine if the desired effect has been achieved. In some embodiments, the ultrasound device may be used to image anatomy after treatment to identify further problem areas or conditions (such as identifying emboli in the anatomy after a procedure). Thus, the method 700 includes switching from treatment mode to IVUS mode to evaluate the effectiveness of ultrasound therapy. The steps 710, 712, and 714 can be repeated as needed to utilize ultrasound for imaging and ultrasound therapy. The method 700 can be completed while the ultrasound device remaining positioned within the anatomy. Advantageously, diagnostic imaging and therapeutic steps can be performed without removing the ultrasound device from the anatomy and inserting other devices.

The method 700 can include treating the diseased area with additional methods if necessary. For example, diseased area of a blood vessel can be dilated using balloon catheter, a correctly sized stent can be positioned inside the blood vessel, and/or drugs can be delivery to the diseased area of the blood vessel. In some embodiments, the additional treatment can be delivered using a therapeutic component of the ultrasound device positioned within the anatomy. In other embodiments, the ultrasound device can be removed and another device can be positioned within anatomy to treat the diseased area. The method 700 can include utilizing the first ultrasound element of the ultrasound device to obtain imaging data of the anatomy, after the additional treatment is complete, to evaluate the effectiveness of the additional treatment.

The systems, devices, and methods of the present disclosure can include features described in U.S. Provisional application Ser. No. 62/545,951, filed on Aug. 16, 2017, U.S. Provisional application Ser. No. 62/545,954, filed on Aug. 15, 2017, U.S. Provisional application Ser. No. 62/545,927, filed on Aug. 15, 2017, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound device configured to be positioned within a lumen of a blood vessel of a patient, the ultrasound device comprising:
an ultrasound processor;
a flexible elongate sheath configured to be positioned within the lumen of the blood vessel of the patient, the sheath comprising an inner lumen;
a rotatable, flexible elongate drive cable comprising a proximal portion and a distal portion, wherein the drive cable is disposed within the inner lumen of the sheath;
a hub coupling the drive cable to the sheath, wherein the hub comprises a rotational interface to permit the drive cable to rotate relative to the sheath;
an ultrasound imaging element disposed at the distal portion of the drive cable and configured to obtain imaging data while the drive cable rotates relative to the sheath, the ultrasound imaging element configured to be controlled by the ultrasound processor;
an ultrasound therapy element disposed at the distal portion of the drive cable and configured to apply an ultrasound therapy while the drive cable rotates relative to the sheath, the ultrasound therapy element configured to be controlled by the ultrasound processor separate from the ultrasound imaging element separately so that the ultrasound therapy applied by the ultrasound therapy element does not interfere with the imaging data obtained by the ultrasound imaging element;
wherein the ultrasound processor is configured to control the ultrasound device to:
acquire ultrasound echoes of the blood vessel using the first ultrasound imaging element;
automatically determine a density or hardness of an occlusion or calcification of the blood vessel based on the acquired ultrasound echoes; and
perform an ultrasound therapy procedure on the occlusion or calcification of the blood vessel based on the determined density or hardness using the ultrasound therapy element.

2. The device of claim 1, wherein the ultrasound imaging element and the ultrasound therapy element each comprise a single transducer.

3. The device of claim 1, wherein a center frequency of the ultrasound imaging element is between 10 MHz and 70 MHz and a center frequency of the ultrasound therapy element is between 20 kHz and 5 MHz.

4. The device of claim 1, wherein the ultrasound imaging element and the ultrasound therapy element are adjacent to one another.

5. The device of claim 1, wherein the hub comprises a port to receive a fluid that fills an inner lumen of the sheath surrounding the drive cable.

6. An ultrasound method for imaging and treating a patient with a device comprising a sheath having an elongate body extending into a lumen of a blood vessel of the patient, and a rotatable, flexible and elongate drive cable disposed within the sheath and coupled to the sheath via a hub, the method comprising:
while the device is inserted into the lumen of the blood vessel of the patient, applying a torque to the drive cable to thereby permit the drive cable to rotate within a rotational interface of the hub;
obtaining imaging data representative of the blood vessel of the patient using a first ultrasound element disposed at a distal portion of the drive cable while the drive cable rotates relative to sheath;
determining a density or hardness of an occlusion or calcification of the blood vessel based on the imaging data representative of the blood vessel of the patient; and
applying an ultrasound therapy to the occlusion or calcification based on the determined density or hardness using a second ultrasound element disposed at the distal portion of the drive cable while the drive cable rotates relative to the sheath;
wherein the obtaining of the imaging data, the determining of the density or hardness of the occlusion or calcification, and the applying of the ultrasound therapy are performed without removing the device from the lumen of the blood vessel of the patient.

7. The method of claim 6, further comprising:
determining, using a computer, a parameter for the ultrasound therapy based on the determined density or hardness.

8. The method of claim 6, wherein the method further comprises introducing a pharmacological agent within the lumen of the blood vessel of the patient.

9. An ultrasound system comprising:
an ultrasound device configured to be positioned within a lumen of a blood vessel of a patient, the ultrasound device comprising: a flexible elongate sheath configured to be positioned within the lumen of the blood vessel of the patient; a rotatable, flexible elongate drive cable disposed within an inner lumen of the sheath and coupled to the sheath via a rotational interface of a hub so that the drive cable is rotatable relative to the sheath; a first ultrasound element disposed at the distal portion of the drive cable and configured to obtain imaging data of the blood vessel while the drive cable rotates relative to the sheath; and a second ultrasound element disposed at the distal portion of the drive cable and configured to apply an ultrasound therapy to the blood vessel while the drive cable rotates relative to the sheath; and a computer in communication with the first and second ultrasound elements, wherein the computer is operable to transmit a plurality of control signals such that the first and second ultrasound elements emit ultrasound energy at a plurality of different frequencies as the drive cable rotates relative to the sheath, the computer programmed to:

acquire ultrasound echoes of the blood vessel using the first ultrasound element;

automatically determine a density or hardness of an occlusion or calcification of the blood vessel based on the acquired ultrasound echoes; and perform an ultrasound therapy procedure on the occlusion or calcification of the blood vessel based on the determined density or hardness using the second ultrasound element.

10. The ultrasound system of claim 9 further comprising a motor coupled to the drive cable and configured to rotate the drive cable relative to the sheath.

11. The ultrasound system of claim 9, wherein the hub comprises a port to receive a fluid that fills the inner lumen of the sheath surrounding the drive cable, wherein the fluid transmits ultrasonic waves and lubricates the rotation of the drive cable relative to the sheath.

* * * * *